United States Patent [19]
Thomas et al.

[11] Patent Number: 6,077,517
[45] Date of Patent: Jun. 20, 2000

[54] HOUSE DUST MITE ALLERGEN, DER P VII, AND USES THEREOF

[75] Inventors: Wayne Robert Thomas, Nedlands; Kaw-Yan Chua, Nollamara, both of Australia

[73] Assignee: ImmuLogic Pharmaceuticals, Inc., Waltham, Mass.

[21] Appl. No.: 08/462,778

[22] Filed: Jun. 5, 1995

Related U.S. Application Data

[60] Division of application No. 08/081,540, Jun. 22, 1993, which is a continuation-in-part of application No. 08/031,141, Mar. 12, 1993, abandoned.

[51] Int. Cl.[7] .............................. A61K 39/35; C07K 1/00
[52] U.S. Cl. .............................. 424/275.1; 514/2; 514/16; 530/328; 530/350
[58] Field of Search .............................. 424/275.1, 276.1, 424/184.1, 185.1; 530/300, 350, 328; 514/16, 2

[56] References Cited

U.S. PATENT DOCUMENTS 4,879,213  11/1989  Fox .............................................. 435/5

FOREIGN PATENT DOCUMENTS 0 473 111 A2  3/1992  European Pat. Off. .

OTHER PUBLICATIONS

Baldo et al. (1989) "Toward a Definition of the 'Complete' Spectrum and Rank Order of Importance of the Allergens from the House Dust Mite: *Dermatophagoides pteronyssinus*" *Adv. BioScience* 74: 13–31.

Bengtsson et al. (1986) "Detection of Allergens in Mould and Mite Preparations by a Nitrocellulose Electroblotting Technique" *Int. Arch. Appl. Immun.* 80: 383–390.

Chapman et al. (1980) "Purification and Characterization of the Major Allergen from Dermatophagoides Pteronyssinus–Antigen P1" *Journal of Immunology* 125(2): 587–592.

Chiba et al. (1990) "Experimental Cedar Pollinosis in Rhesus Monkeys" *Int. Arch. Allergy Appl. Immunol.* 93: 83–88.

Chua et al. (1990) "Expression of Dermatophagoides Pteronyssinus Allergen, Der pII, in *Escherichia coli* and the Binding Studies with Human IgE" *Int. Arch. Allergy Appl. Immunol.* 91: 124–129.

Ford et al. (1990) "The Spectrum of Low Molecular Weight House Dust Mite (Dermatophagoides Pteronyssinus) Allergens with Emphasis on Der p II" *Clinical and Experimental Allergy* 20(1): 27–31.

Greene et al. (1990) "Antigenic Analysis of Group i House Dust Mite Allergens Using Random Fragments of Der p i Expressed by Recombinant DNA Libraries" *Int. Arch. Appl. Allergy Immunol.* 92: 30–38.

Greene et al. (1992) "IgE Binding Structures of the Major House Dust Mite Allergen Der P I" *Molecular Immunology* 29(2): 25777–262.

King et al. (1976) "Chemical and Biological Properties of Some Atopic Allergens" *Advances in Immunology* 23: 77–105.

Kohmoto et al. (1991) "Activation of the Kallikren–Kinn System in Human Plasma by a Scrine Protease from Mites" *Journal Clin. Biochem. Nutr.* 10: 15–20.

Lind et al. (1983) "Identification of Allergens in *Dermatophagoides pteronyssinus* Mite Body Extract by Crossed Radioimmunoelectrophoresis with Two Different Rabbit Antibody Pools" *Scand. J. Immunol.* 17: 263–273.

Lind (1985) "Purification and Partial Characterization of Two Major Allergens from the House Dust Mite Dermatophagoides Pteronyssinus" *Journal of Allergy and Clinical Immunology* 76(5): 753–761.

Stewart et al. (1992) "The Group III Allergen from the House Dust Mite Dermatophagoides Pteronyssinus is a Trypsin–like Enzym" *Immunology* 75: 29–35.

Stewart et al. (1988) "Standardization of Rye–Grass Pollen (lolium perenne) Extract" *Int. Arch. Allergy Appl. Immun.* 86: 9–18.

Thomas et al. (1988) "Cloning and Expression of DNA Coding for the Major House Dust Mite Allergen Der p 1 in *Escherichia coli*" *Int. Arch. Allergy Appl. Immun.* 85: 127–129.

Tovey et al. (1989) "The Cloning of a Mite (Dermatophagoides Pteronyssinus) Recombinant Protein that Shares IgE—Binding Determinants with a 14–15KD Component of Mite Extracts" *Advances in Biosciences* 74: 33–43.

Tovey et al. (1987) "Comparison by Electroblotting of IgE–binding Components in Extracts of House Dust Mite Bodies and Spent Mite Culture" *Journal of Allergy and Clinical Immunology* 79(1): 93–102.

Van der Zee et al. (1988) "Skin Tests and Histamine Release with P1–depleted Dermatophagoides Pteronyssinus Body Extracts and Purified P1" *Journal of Allergy and Clinical Immunology* 81(5): 884–896.

Yuuki et al. (1991) "Cloning and Expression of cDNA Coding for the Major House Dust Mite Allergen Derf II in *Escherichia coli*" *Agric. Biol. Chem.* 55(5): 1233–1238.

Critical Synergy: The Biotechnology Industry and Intellectual Property Protection, Presentation of the Intellectual Property Committee of the Biotechnology Industry Organization at the Oct. 17, 1994, Hearing of the U.S. Patent and Trademark Office, San Diego, CA, published by the Biotechnology Industry Organization, Washington, D.C. pp. 75 and 100–107.

(List continued on next page.)

*Primary Examiner*—Patricia A. Duffy
*Attorney, Agent, or Firm*—Lahive & Cockfield, LLP; Amy E. Mandragouras, Esq.; Jane E. Remillard, Esq.

[57] ABSTRACT

A novel protein allergen Der p VII of *Dennatophagoides pteronyssinus* is described. A cDNA clone encoding Der p VII was isolated from a λgt11 library of *D. pteronyssinus* cDNA. The nucleic acid sequence of der p VII encodes a 198 residue mature processed protein having a predicted molecular weight of 22,177 daltons. Der p VII protein may be used as the active ingredient in therapeutic composition for the treatment of sensitivity to house dust mites. The protein may also be used in methods of diagnosing such sensitivity.

14 Claims, 5 Drawing Sheets

OTHER PUBLICATIONS

Shen, H. et al., "Molecular cloning of a house dust mite allergen with common antibody binding specificities with multiple components in mite extracts", *Clinical and Experimental Allergy*, vol. 23, pp. 934–940 (1993).

Burgess et al. J. Cell Biology III:2129–2137 1990.

Lozar et al. Mol. and Cellular Biology 8(3):1247–52 1988.

Kumar et al. PNAS 87:1337–1341 1990.

Bowie et al. Science 247:1306–1310 1990.

Stewart et al. Int. Arch Allergy App. Immunology 69(3):224–230 1982.

Stewart et al. Aust. J. Exp. Biol. Med. Sci 58(3):259–74 1980.

Abe et al. Allergy 42(5):352–358 1977.

Hoyne et al. Immunology 78(1):65–73 Jan. 1993

Roitt et al. *Immunology* Gower Medical Publishing Company (New York) 1985 p. 19.2.

Terr A.I. "Allergic Diseases" in Basic Clinical Immunology 6th Edition, Stites et al. Eds Appleton and Lang (Norwalk CN) 1987 pp. 435 and 442.

```
TTTTTTTTTTTTTGGTTATTCCCATTTTTTTCATATCGTAAAAATCCAAATTCACTTTT  60

TTACCAA ATG ATG AAA TTA TTA TTG ATT GCT GCC GCA GCT TTT GTT  106
        Met Met Lys Leu Leu Leu Ile Ala Ala Ala Ala Phe Val

GCC GTT TCG GCT GAT CCA ATT CAC TAT GAT AAA ATC ACC GAA GAA  151
Ala Val Ser Ala Asp Pro Ile His Tyr Asp Lys Ile Thr Glu Glu

ATT AAC AAA GCT GTT GAT GAA GCC GTC GCT GCA ATT GAA AAA TCC  196
Ile Asn Lys Ala Val Asp Glu Ala Val Ala Ala Ile Glu Lys Ser

GAA ACA TTC GAT CCA ATG AAG GTA CCC GAT CAT TCT GAT AAA TTC  241
Glu Thr Phe Asp Pro Met Lys Val Pro Asp His Ser Asp Lys Phe

GAA CGA CAT ATT GGT ATC ATC GAT TTA AAA GGT GAA TTA GAC ATG  286
Glu Arg His Ile Gly Ile Ile Asp Leu Lys Gly Glu Leu Asp Met

CGA AAC ATT CAA GTT CGA GGA TTA AAA CAA ATG AAA CGT GTA GGT  331
Arg Asn Ile Gln Val Arg Gly Leu Lys Gln Met Lys Arg Val Gly

GAT GCT AAT GTG AAA AGT GAA GAT GGT GTT GTC AAA GCT CAT TTG  376
Asp Ala Asn Val Lys Ser Glu Asp Gly Val Val Lys Ala His Leu

TTG GTC GGT GTT CAT GAT GAC GTT GTT TCA ATG GAA TAT GAT TTA  421
Leu Val Gly Val His Asp Asp Val Val Ser Met Glu Tyr Asp Leu

GCA TAC AAA TTG GGT GAT CTT CAT CCA AAC ACT CAT GTC ATT TCG  466
Ala Tyr Lys Leu Gly Asp Leu His Pro Asn Thr His Val Ile Ser

GAT ATT CAG GAT TTT GTT GTC GAA TTA TCG CTC GAA GTT AGC GAA  511
Asp Ile Gln Asp Phe Val Val Glu Leu Ser Leu Glu Val Ser Glu

GAA GGT AAT ATG ACA TTG ACA TCG TTC GAA GTA CGT CAA TTT GCC  556
Glu Gly Asn Met Thr Leu Thr Ser Phe Glu Val Arg Gln Phe Ala

AAT GTT GTC AAT CAT ATT GGT GGT CTT TCA ATT TTG GAT CCA ATT  601
Asn Val Val Asn His Ile Gly Gly Leu Ser Ile Leu Asp Pro Ile

TTC GCT GTC TTA TCC GAT GTT TTG ACC GCT ATT TTC CAG GAT ACC  646
Phe Ala Val Leu Ser Asp Val Leu The Ala Ile Phe Gln Asp Thr

GTA CGT GCA GAA ATG ACC AAA GTA TTG GCA CCA GCA TTC AAA AAA  691
Val Arg Ala Glu Met Thr Lys Val Leu Ala Pro Ala Phe Lys Lys

GAA TTG GAA CGA AAC AAC CAA TAGACTTACACACAACATAACACTGTTATTT  743
Glu Leu Glu Arg Asn Asn Gln

TTACACTGGATAATCAAATGAAATAAATTTTTTTATCATTTTGTTTAAAAAAAAAAAAA  802

AAAAAAAAAA  812
```

Fig. 3

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 812 base pairs
      (B) TYPE: nucleic acid (C) STRANDEDNESS: single
(D) TOPOLOGY: linear (ii) MOLECULE TYPE: cDNA (ix) FEATURE:
(A) NAME/KEY: CDS
(B) LOCATION: 68..712

(xi) SEQUENCE DESCRIPTION: SEQ ID NO:1:

```
TTTTTTTTTT TTTTGGTTAT TCCCATTTTT TTCATATCGT AAAAATCCAA ATTCACTTTT        60

TTACCAA ATG ATG AAA TTA TTA TTG ATT GCT GCC GCA GCT TTT GTT GCC         109
        Met Met Lys Leu Leu Leu Ile Ala Ala Ala Ala Phe Val Ala
        1               5                   10

GTT TCG GCT GAT CCA ATT CAC TAT GAT AAA ATC ACC GAA GAA ATT AAC         157
Val Ser Ala Asp Pro Ile His Tyr Asp Lys Ile Thr Glu Glu Ile Asn
15                  20                  25                  30

AAA GCT GTT GAT GAA GCC GTC GCT GCA ATT GAA AAA TCC GAA ACA TTC         205
Lys Ala Val Asp Glu Ala Val Ala Ala Ile Glu Lys Ser Glu Thr Phe
                35                  40                  45

GAT CCA ATG AAG GTA CCC GAT CAT TCT GAT AAA TTC GAA CGA CAT ATT         253
Asp Pro Met Lys Val Pro Asp His Ser Asp Lys Phe Glu Arg His Ile
            50                  55                  60

GGT ATC ATC GAT TTA AAA GGT CAA TTA GAC ATG CGA AAC ATT CAA GTT         301
Gly Ile Ile Asp Leu Lys Gly Gln Leu Asp Met Arg Asn Ile Gln Val
            65                  70                  75

CGA GGA TTA AAA CAA ATG AAA CGT GTA GGT GAT GCT AAT GTG AAA AGT         349
Arg Gly Leu Lys Gln Met Lys Arg Val Gly Asp Ala Asn Val Lys Ser
80                  85                  90

GAA GAT GGT GTT GTC AAA GCT CAT TTG TTG GTC GGT GTT CAT GAT GAC         397
Glu Asp Gly Val Val Lys Ala His Leu Leu Val Gly Val His Asp Asp
95                  100                 105                 110

GTT GTT TCA ATG GAA TAT GAT TTA GCA TAC AAA TTG GGT GAT CTT CAT         445
Val Val Ser Met Glu Tyr Asp Leu Ala Tyr Lys Leu Gly Asp Leu His
                115                 120                 125

CCA AAC ACT CAT GTC ATT TCG GAT ATT CAG GAT TTT GTT GTC GAA TTA         493
Pro Asn Thr His Val Ile Ser Asp Ile Gln Asp Phe Val Val Glu Leu
            130                 135                 140

TCG CTC GAA GTT AGC GAA GAA GGT AAT ATG ACA TTG ACA TCG TTC GAA         541
Ser Leu Glu Val Ser Glu Glu Gly Asn Met Thr Leu Thr Ser Phe Glu
            145                 150                 155

GTA CGT CAA TTT GCC AAT GTT GTC AAT CAT ATT GGT GGT CTT TCA ATT         589
Val Arg Gln Phe Ala Asn Val Val Asn His Ile Gly Gly Leu Ser Ile
160                 165                 170

TTG GAT CCA ATT TTC GCT GTC TTA TCC GAT GTT TTG ACC GCT ATT TTC         637
Leu Asp Pro Ile Phe Ala Val Leu Ser Asp Val Leu Thr Ala Ile Phe
175                 180                 185                 190

CAG GAT ACC GTA CGT GCA GAA ATG ACC AAA GTA TTG GCA CCA GCA TTC         685
Gln Asp Thr Val Arg Ala Glu Met Thr Lys Val Leu Ala Pro Ala Phe
                195                 200                 205

AAA AAA GAA TTG GAA CGA AAC AAC CAA TAGACTTACA CACAACATAA               732
Lys Lys Glu Leu Glu Arg Asn Asn Gln
            210                 215

CACTGTTATT TTTACACTGG ATAATCAAAT GAAATAAATT TTTTATCAT TTGTTTAAA         792

AAAAAAAAAA AAAAAAAAA                                                    812
```

(2) INFORMATION FOR SEQ ID NO:2:

(i) SEQUENCE CHARACTERISTICS:
(A) LENGTH: 215 amino acids
(B) TYPE: amino acid (D) TOPOLOGY: linear (ii) MOLECULE TYPE: protein (xi) SEQUENCE DESCRIPTION: SEQ ID NO:2:

Met Met Lys Leu Leu Leu Ile Ala Ala Ala Phe Val Ala Val Ser
 1               5                  10                  15

Ala Asp Pro Ile His Tyr Asp Lys Ile Thr Glu Glu Ile Asn Lys Ala
             20                  25                  30

Val Asp Glu Ala Val Ala Ala Ile Glu Lys Ser Glu Thr Phe Asp Pro
         35                  40                  45

Met Lys Val Pro Asp His Ser Asp Lys Phe Glu Arg His Ile Gly Ile
     50                  55                  60

Ile Asp Leu Lys Gly Gln Leu Asp Met Arg Asn Ile Gln Val Arg Gly
 65                  70                  75                  80

Leu Lys Gln Met Lys Arg Val Gly Asp Ala Asn Val Lys Ser Glu Asp
                 85                  90                  95

Gly Val Val Lys Ala His Leu Leu Val Gly Val His Asp Asp Val Val
            100                 105                 110

Ser Met Glu Tyr Asp Leu Ala Tyr Lys Leu Gly Asp Leu His Pro Asn
        115                 120                 125

Thr His Val Ile Ser Asp Ile Gln Asp Phe Val Val Glu Leu Ser Leu
        130                 135                 140

Glu Val Ser Glu Glu Gly Asn Met Thr Leu Thr Ser Phe Glu Val Arg
145                 150                 155                 160

Gln Phe Ala Asn Val Val Asn His Ile Gly Gly Leu Ser Ile Leu Asp
                165                 170                 175

Pro Ile Phe Ala Val Leu Ser Asp Val Leu Thr Ala Ile Phe Gln Asp
            180                 185                 190

Thr Val Arg Ala Glu Met Thr Lys Val Leu Ala Pro Ala Phe Lys Lys
        195                 200                 205

Glu Leu Glu Arg Asn Asn Gln
    210                 215

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

GATCCAATTC ACTATGAT                                            18

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

GGTGAATTAG ACATGCG                                             17

```
(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

TCAATTTTGG ATCCAATTTT CGCT                                        24
```

HOUSE DUST MITE ALLERGEN, DER P VII, AND USES THEREOF

RELATED U.S. APPLICATION DATA

This application is a divisional application of Ser. No. 08/081,540 filed on Jun. 22, 1993, pending, which in turn is a continuation-in-part application of Ser. No. 08/031,141 filed on Mar. 12, 1993, abandoned. The contents of all of the aforementioned application(s) are hereby incorporated by reference.

BACKGROUND OF INVENTION

Approximately 10% of the population become hypersensitized (allergic) upon exposure to antigens from a variety of environmental sources. Those antigens that induce immediate and/or delayed types of hypersensitivity are known as allergens (King, T. P., (1976) *Adv. Immunol.*, 2:77–105). These include products of grasses, trees, weeds, animal dander, insects, food, drugs, and chemicals. Genetic predisposition of an individual is believed to play a role in the development of immediate allergic responses (Young, R. P. t al., (1990) *Clin. Sci.*, 79:19) such as atopy and anaphylaxis whose symptoms include hay fever, asthma, and hives.

The antibodies involved in atopic allergy belong primarily to the IgE class of immunoglobins. IgE binds to basophils, mast cells and dendritic cells via a specific, high-affinity receptor FceRI (Kinet, J. P., (1990) *Curr. Opin. Immunol.*, 2:499–505). Upon combination of an allergen acting as a ligand with its cognate receptor IgE, FceRI bound to the IgE may be cross-linked on the cell surface, resulting in physiological manifestations of the IgE-allergen interaction. These physiological effects include the release of, among other substances, histamine, serotonin, heparin, chemotactic factor(s) for eosinophilic leukocytes and/or leukotrienes C4, D4, and E4, which cause prolonged constriction of bronchial smooth muscle cells (Hood, L. E. et al., *Immunology* (2nd ed.), The Benjamin/Cumming Publishing Co., Inc. (1984)). Hence, the ultimate consequence of the interaction of an allergen with IgE is allergic symptoms triggered by the release of the aforementioned mediators. Such symptoms may be systemic or local in nature, depending on the route of entry of the antigen and the pattern of deposition of IgE on mast cells or basophils. Local manifestations generally occur on epithelial surfaces at the site of entry of the allergen. Systemic effects can induce anaphylaxis (anaphylactic shock) which results from IgE-basophil response to circulating (intravascular) antigen.

Studies with purified allergens have shown that about 80% of patients allergic to the mite *Dermatophagoides pteronyssinus* produce IgE reactive to Der p I and Der p II (Chapman M. D. et al., *J. Immunol.* (1980) 125:587–92; Lind P., *J. Allergy Clin. Immunol.* (1985) 7:753–61; Van derZee J. S. et al., *J. Allergy Clin. Immunol.* (1988) 81:884–95). For about half the patients these specificities constitute 50% of the IgE antimite antibody. The allergen Der p III recently identified as trypsin (Stewart G. A. et al., *Immunology* (1992) 75:29–35) reacts with a similar or higher frequency (Stewart G. A. et al., supra; Ford S. A. et al. *Clin. Exp. Allergy* (1989) 2:27–3 1). However, in the only quantitative study performed to date, the investigators reported the level of IgE binding to be considerably less than Der p I. Electrophoretic techniques (Ford S. A. et al., sulpra; Bengtsson A. et al., *Int. Arch. Allergy Appl. Immunol.* (1986) 80:383–90; Lind P. et al., *Scand. J. Immunol.* (1983) 11:263–73; Tovey E. R. et al., *J. Allergy Clin. Immunol.* (1987) 79:93–102) have shown that most sera recognize other allergens. For example, in the study of Ford et al. (supra) Western blotting showed 8 sera reacting with 1–2 bands, 6 with 3–6 and 3 with a greater number including one with at least 13. In another study, Baldo et al. (*Adv. Bioscience*(1989)4:13–31) report the finding of components at Mr 30, 26, 25K reacting with 50% of sera. To determine the importance of particular specificities in the allergic reactions, purified allergens would be required for quantitative IgE binding tests and to examine the frequency and lymphokine profile for T cell reactivity.

Treatment of patients with sensitivity to house dust mites by administration of increasing doses of house dust extracts has the drawbacks of potential anaphylaxis during treatment and the possible necessity of continuing therapy over a period of several years to build up sufficient tolerance that results in significant diminution of clinical symptoms. A therapeutic composition and method of therapy which avoids these problems would be beneficial.

SUMMARY OF INVENTION

The present invention provides nucleic acid sequences coding for HD6, a clone isolated from a λgt11 expression library of *Dennatophagoides pteroniyssinus* (House dust mite) CDNA. Clone HD6 encodes a novel allergen of *D. pteronyssinus*, Der p VII. The present invention also provides isolated Der p VII protein produced in a host cell transformed with a nucleic acid vector directing the expression of a nucleotide sequence coding for Der p VII, and Der p VII prepared by chemical synthesis.

Other aspects of the invention include purified Der p VII protein and antibodies specifically reactive with the Der p VII protein. Der p VII protein may be used as the active ingredient in therapeutic compositions for use in treating and preventing allergic sensitivity to house dust mites. Der p VII protein is also useful for diagnosing sensitivity to house dust mites in an individual.

BRIEF DESCRIPTION OF THE DRAWINGS

FIG. 3 is the nucleotide sequence and deduced amino acid sequence of clone HD6.

DETAILED DESCRIPTION OF THE INVENTION

Figure 1:
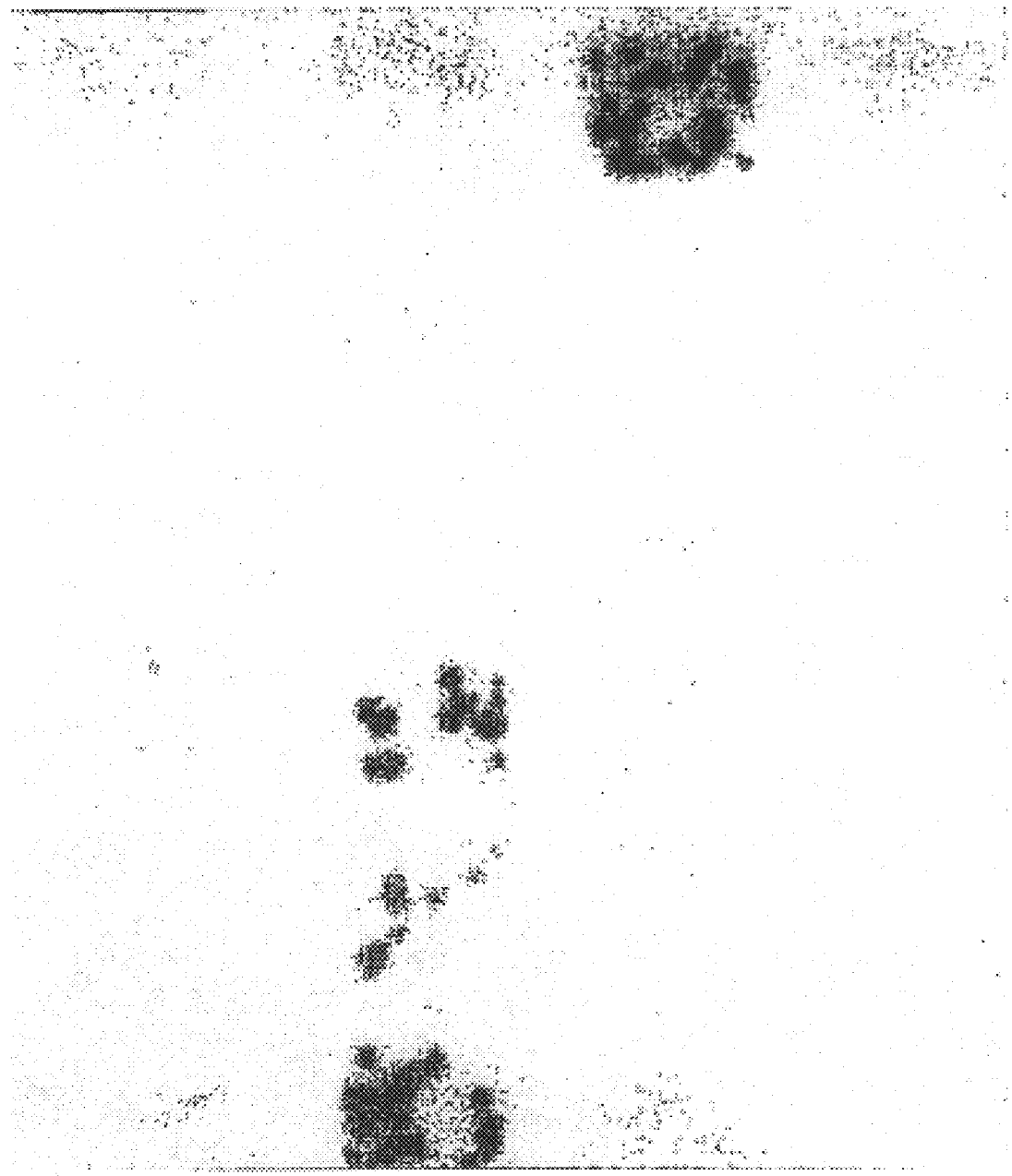
FIG. 1 shows the binding frequency of IgE from allergic sera with λgt11-HD6 plaques.

The present invention pertains to nucleic acid sequences coding for HD6, a cDNA clone encoding a *Dermatophagoides pteronyssinus* allergen, Der p VII, that reacts with about 40% of mite allergic sera. Plaque radioimmune assay was used to isolate HD6, a clone from a λgt11 library of *D. pteronyssinus* cDNA which encodes an IgE-binding protein. A nucleic acid sequence coding for Der p VII preferably has the sequence shown in FIG. 3 (SEQ ID NO: 1). The nucleic acid sequence coding for Der p VII contains a predicted 17 amino acid residue leader sequence (encoded by base 68 through base 118). This leader sequence is not found in the mature Der p VII protein which is encoded by bases 119 through 715. The deduced amino acid sequence of Der p VII is also shown in FIG. 3 (SEQ ID NO: 2). The nucleic acid sequence of Der p VII encodes a 198 residue mature, processed protein having a predicted molecular weight of 22,177 daltons, no cysteines and a single potential N-linked glycosylation site. N-linked glycosylation may increase the molecular weight of the mature protein. A termination codon TAG was followed 49 nucleotides later by a polyadenylation site and a poly A tail (see FIG. 3). A host cell transformed with a vector containing a nucleic acid sequence coding for Der p VII has been deposited with the American Type Culture Collection at accession number 69348.

Accordingly, one aspect of the present invention pertains to an isolated nucleic acid having a nucleotide sequence coding for Der p VII, fragments thereof or equivalents thereof. The term nucleic acid as used herein is intended to include such fragments or equivalents. A nucleic acid sequence coding for Der p VII may be obtained from mRNA present in house dust mites of the species D. pteronyssinus. It should also be possible to obtain nucleic acid sequences coding for Der p VII from mite genomic DNA. The nucleic acid sequence coding for Der p VII may be obtained using the method disclosed herein or any other suitable technique for isolation and molecular cloning of genes. The nucleic acid sequences of the invention may be DNA or RNA. The preferred nucleic acid is a cDNA having the sequence depicted in FIG. 3 or equivalents thereof.

The term equivalent is intended to include nucleotide sequences coding for functionally equivalent Der p VII proteins. For example, DNA sequence polymorphisms within the nucleotide sequence of Der p VII (especially those within the third base of a codon) may result in "silent" mutations which do not affect the amino acid sequence of the Der p VII protein. However, it is expected that DNA sequence polymorphisms that do lead to changes in the amino acid sequence of Der p VII will exist within the house dust mite population. It will be appreciated by one skilled in the art that these variations in one or more nucleotides (up to about 3–4% of the nucleotides) of the nucleic acid sequence coding for Der p VII may exist among individual house dust mites due to natural allelic variation. Any and all such nucleotide variations and resulting amino acid polymorphisms are within the scope of the invention. Furthermore, there may be one or more isoforms or related, cross-reacting family members of Der p VII. Such isoforms or family members are defined as proteins related in function and amino acid sequence to Der p VII, but encoded by genes at different loci.

A fragment of the nucleic acid sequence coding for Der p VII is defined as a nucleotide sequence having fewer nucleotides than the nucleotide sequence coding for the entire amino acid sequence of Der p VII protein. Such fragments may encode an antigenic fragment of Der p VII protein which induces an immune response in mammals, preferably humans, such as stimulating production of minimal amounts of IgE, binding of IgE, eliciting the production of IgG and IgM antibodies, or eliciting a T cell response such as proliferation and/or lymphokine secretion and/or induction of T cell anergy. Nucleic acid fragments within the scope of the invention include those capable of hybridizing with nucleic acid from other animal species for use in screening protocols to detect Der p VII or allergens that are cross-reactive with Der p VII. Generally, the nucleic acid sequence coding for an antigenic fragment or fragments of Der p VII will be selected from the bases coding for the mature protein, however, in some instances it may be desirable to select all or part of a fragment or fragments from the leader sequence portion of the nucleic acid sequence of the invention. Nucleic acid sequences within the scope of the invention may also contain linker sequences, modified restriction endonuclease sites and other sequences useful for molecular cloning, expression or purification of recombinant Der p VII or fragments thereof.

The present invention also provides expression vectors containing a nucleic acid sequence coding for Der p VII, operably linked to at least one regulatory sequence. Operably linked is intended to mean that the nucleotide acid sequence is linked to a regulatory sequence in a manner which allows expression of the nucleotide sequence. Regulatory sequences are art-recognized and are selected to direct expression of Der p VII. Accordingly, the term regulatory sequence includes promoters, enhancers and other expression control elements. Such regulatory sequences are described in Goeddel, *Gene Expression Technology: Methods in Enzymology* 185, Academic Press, San Diego, Calif. (1990)). It should be understood that the design of the expression vector may depend on such factors as the choice of the host cell to be transformed and/or the type of protein desired to be expressed.

This invention further pertains to a host cell transformed to express Der p VII. The host cell may be any procaryotic or eucaryotic cell. For example, Der p VII protein may be expressed in bacterial cells such as *E. coli*, insect cells (baculovirus), yeast, or mammalian cells such as Chinese hamster ovary cells (CHO). Other suitable host cells may be found in Goeddel, (1990) supra or known to those skilled in the art.

Expression in eucaryotic cells such as mammalian, yeast, or insect cells can lead to partial or complete glycosylation and/or formation of relevant inter- or intra-chain disulfide bonds of recombinant protein. Examples of vectors for expression in yeast *S. cerivisae* include pYepSec1 (Baldari. et al., (1987) *Embo J.* 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.). Baculovirus vectors available for expression of proteins in cultured insect cells (SF 9 cells) include the pAc series (Smith et al., (1983) *Mol. Cell Biol.*3:2156–2165) and the pVL series (Lucklow, V. A., and Summers, M. D., (1989) *Virology* 117:31–39). Generally COS cells (Gluzman, Y., (1981) *Cell* 23:175–182) are used in conjunction with such vectors as pCDM 8 (Aruffo, A. and Seed, B., (1987) *Proc. Natl. Acad. Sci. USA* 84:8573–8577) for transient amplification/expression in mammalian cells, while CHO (dhfr⁻ Chinese Hamster Qvary) cells are used with vectors such as pMT2PC (Kaufman e al (1987), *EMBO J.* 6:187–195) for stable amplification/expression in mammalian cells. Vector DNA can be introduced into mammalian cells via conventional techniques such as calcium phosphate or calcium chloride co-precipitation, DEAE-dextran-mediated transfection, or electroporation. Suitable methods for transforming host cells can be found in Sambrook et al. (*Molecular Cloning: A Laboratory Manual*, 2nd Edition, Cold Spring Harbor Laboratory press (1989)), and other laboratory textbooks.

Expression in procaryotes is most often carried out in *E. coli* with either fusion or non-fusion inducible expression vectors. Fusion vectors usually add a number of NH$_2$ terminal amino acids to the expressed target gene. These NH$_2$ terminal amino acids often are referred to as a reporter group. Such reporter groups usually serve two purposes: 1) to increase the solubility of the target recombinant protein; and 2) to aid in the purification of the target recombinant protein by acting as a ligand in affinity purification. Often, in fusion expression vectors, a proteolytic cleavage site is introduced at the junction of the reporter group and the target recombinant protein to enable separation of the target recombinant protein from the reporter group subsequent to purification of the fusion protein. Such enzymes, and their cognate recognition sequences, include Factor Xa, thrombin and enterokinase. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-tranferase, maltose E binding protein, or protein A, respectively, to the target recombinant protein.

Inducible non-fusion expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). While target gene expression relies on host RNA polymerase transcription from the hybrid trp-lac fusion promoter in pTrc, expression of target genes inserted into pET 11d relies on transcription from the T7 gn10-lac 0 fusion promoter mediated by coexpressed viral RNA polymerase (T7 gn1). This viral polymerase is supplied by host strains BL21 (DE3) or HMS174(DE3) from a resident λ prophage harboring a T7 gn1 under the transcriptional control of the lacUV 5 promoter.

One strategy to maximize recombinant Der p VII expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy would be to alter the nucleic acid sequence of the Der p VII gene to be inserted into an expression vector so that the individual codons for each amino acid would be those preferentially utilized in highly expressed *E. coli* proteins (Wada et al., (1992) *Nuc. Acids Res.* 20:2111–2118). Such alteration of nucleic acid sequences of the invention could be carried out by standard DNA synthesis techniques.

The nucleic acid sequences of the invention can also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

The present invention further pertains to methods of producing Der p VII protein. For example, a host cell transformed with a nucleic acid vector directing expression of a nucleotide sequence coding for Der p VII protein can be cultured under appropriate conditions to allow expression of Der p VII to occur. The protein may be secreted and isolated from a mixture of cells and medium containing Der p VII protein. Alternatively, the protein may be retained cytoplasmically and the cells harvested, lysed and the protein isolated. The culture includes host cells, media and other byproducts. Suitable mediums for cell culture are well known in the art. Der p VII protein can be isolated from cell culture medium, host cells, or both using techniques known in the art for purifying proteins including ion-exchange chromatography, gel filtration chromatography, ultrafiltration, electrophoresis, and immunoaffinity purification with antibodies specific for Der p VII or fragment thereof.

Another aspect of the invention pertains to isolated Der p VII protein. The term "Der p VII" or "Der p VII protein" is intended to include functional equivalents thereof and antigenic fragments thereof. The term functional equivalent is intended to include proteins which differ in amino acid sequence from the Der p VII sequence depicted in FIG. 3 (SEQ ID NO:2) but where such differences result in a modified protein which functions in the same or similar manner as Der p VII or which has the same or similar characteristics of Der p VII. For example, a functional equivalent of Der p VII may have a modification such as a substitution, addition or deletion of an amino acid residue which is not directly involved in the antigenicity of Der p VII (i.e., the ability of Der p VII to induce an immune response in a mammal, such as stimulating production of minimal amounts of IgE, binding of IgE, eliciting the production of IgG and IgM antibodies, or eliciting a T cell response such as proliferation and/or lymphokine secretion and/or induction of T cell anergy, IgE reactivity or T cell reactivity). In addition, non-naturally occurring analogues of Der p VII having T cell stimulating activity and a greater degree of homology with Der p VII than other *Dermatophagoides pteronyssinus* allergens are considered functional equivalents. Various modifications of the Der p VII protein to produce functional equivalents of Der p VII are described in detail herein.

The term isolated as used herein refers to Der p VII protein substantially free of cellular material or culture medium when produced by recombinant DNA techniques, or chemical precursors or other chemicals when chemically synthesized. Such Der p VII protein is also characterized as being free of all other mite proteins. Accordingly, an isolated Der p VII protein is produced recombinantly or synthetically and is substantially free of cellular material and culture medium or substantially free of chemical precursors or other chemicals and is free of all other mite proteins.

Fragments of Der p VII eliciting a desired antigenic response (referred to herein as antigenic fragments) may be obtained, for example, by screening peptides recombinantly produced from the corresponding fragment of the nucleic acid sequence of Der p VII coding for such peptides. In addition, fragments can be chemically synthesized using techniques known in the art such as conventional Merrifield solid phase f-Moc or t-Boc chemistry. For example, the Der p VII protein may be arbitrarily divided into fragments of desired length with no overlap of the fragments, or preferably divided into overlapping fragments of a desired length. The fragments can be produced (recombinantly or by chemical synthesis) and tested to determine their antigenicity (i.e., the ability of the fragment to induce an immune response in a mammal). If fragments of Der p VII are to be used for therapeutic purposes, then fragments which are capable of eliciting a T-cell response, such as stimulation (i.e., proliferation or lymphokine secretion) and/or are capable of inducing T-cell anergy are particularly desirable.

Antigenic fragments of Der p VII which have minimal IgE synthesis stimulating activity are also desirable. Minimal IgE stimulating activity refers to IgE stimulating activity that is less than the amount of IgE production elicited by purified, native Der p VII protein. For therapeutic purposes, isolated Der p VII and antigenic fragments thereof, preferably do not bind IgE specific for a house dust mite allergen, or bind such IgE to a substantially lesser extent than the purified native house dust mite allergen binds such IgE. If the isolated Der p VII or fragment thereof binds IgE, it is preferable that such binding does not result in the release of mediators (e.g., histamines) from mast cells or basophils.

The isolated Der p VII protein or fragments thereof are preferably tested in mammalian models of house dust mite atopy, such as the mouse model disclosed in Tamura et al., (1986) *Microbiol. Immunol.* 30:883–896, or in U.S. Pat. No. 4,939,239, or in the primate model disclosed in Chiba et al., (1990) *Int. Arch. Allergy Immunol.* 9:83–88. Initial screening for IgE binding to the Der p VII protein or fragments thereof may be performed by scratch tests or intradermal skin tests on laboratory animals or human volunteers, or in in vitro systems such as RAST, RAST inhibition, ELISA assay, RIA (radioimmunoassay), or histamine release.

Isolated antigenic fragments of Der p VII which have T-cell stimulating activity, and thus comprise at least one T-cell epitope are also particularly desirable for therapeutic purposes. T-cell epitopes are believed to be involved in initiation and perpetuation of the immune response to the protein allergen which is responsible for the clinical symptoms of allergy. These T-cell epitopes are thought to trigger early events at the level of the T helper cell by binding to an appropriate HLA molecule on the surface of an antigen presenting cell, thereby stimulating the T-cell subpopulation with the relevant T-cell receptor for the epitope. These events lead to T-cell proliferation, lymphokine secretion, local inflammatory reactions, recruitment of additional immune cells to the site of antigen/T-cell interaction, and activation of the B-cell cascade, leading to the production of antibodies. One isotype of these antibodies, IgE, is fundamentally important to the development of allergic symptoms and its production is influenced early in the cascade of events at the level of the T helper cell, by the nature of the lymphokines secreted. A T-cell epitope is the basic element, or smallest unit of recognition by a T-cell receptor, where the epitope comprises amino acids essential to receptor recognition. Amino acid sequences which mimic those of the T-cell epitopes and which modify the allergic response to protein allergens are within the scope of this invention.

Exposure of allergic individuals to isolated Der p VII or an antigenic fragment having T cell stimulating activity, may tolerize or anergize appropriate T-cell subpopulations such that they become unresponsive to the protein allergen and do not participate in stimulating an immune response upon such exposure. In addition, such administration may modify the lymphokine secretion profile as compared with exposure to the naturally-occurring protein allergen or portion thereof (e.g., result in a decrease of IL-4 and/or an increase in IL-2). Furthermore, exposure to the Der p VII protein or antigenic fragment having T cell stimulating activity may influence T-cell subpopulations which normally participate in the response to the allergen such that these T-cells are drawn away from the site(s) of normal exposure to the allergen (e.g., nasal mucosa, skin, and lung) towards the site(s) of therapeutic administration of the protein or fragment derived therefrom. This redistribution of T-cell subpopulations may ameliorate or reduce the ability of an individual's immune system to stimulate the usual immune response at the site of normal exposure to the allergen, resulting in a diminution in allergic symptoms.

It is possible to modify the structure of the Der p VII protein for such purposes as increasing solubility, enhancing therapeutic or prophylactic efficacy, or stability (e.g., shelf life ex vivo and resistance to proteolytic degradation in vivo). Such modified proteins are considered functional equivalents of the Der p VII protein as defined herein. A modified protein can be produced in which the amino acid sequence has been altered, such as by amino acid substitution, deletion, or addition, to modify immunogenicity and/or reduce allergenicity, or to which a component has been added for the same purpose.

For example, the Der p VII protein can be modified so that it maintains the ability to induce T-cell anergy and bind MHC proteins without the ability to induce a strong proliferative response or possibly, any proliferative response when administered in immunogenic form. In this instance, critical binding residues for T cell receptor function can be determined using known techniques (e.g., substitution of each residue and determination of the presence or absence of T-cell reactivity). Those residues shown to be essential to interact with the T-cell receptor can be modified by replacing the essential amino acid with another, preferably similar amino acid residue (a conservative substitution) whose presence is shown to enhance, diminish, but not eliminate, or not effect T-cell reactivity. In addition, those amino acid residues which are not essential for T-cell receptor interaction can be modified by being replaced by another amino acid whose incorporation may enhance, diminish, or not effect T-cell reactivity, but does not eliminate binding to relevant MHC.

Additionally, the Der p VII can be modified by replacing an amino acid shown to be essential to interact with the MHC protein complex with another, preferably similar amino acid residue (conservative substitution) whose presence is shown to enhance, diminish, but not eliminate or effect T-cell activity. In addition, amino acid residues which are not essential for interaction with the MHC protein complex but which still bind the MHC protein complex can be modified by being replaced by another amino acid whose incorporation may enhance, not effect, or diminish but not eliminate T-cell reactivity. Preferred amino acid substitutions for non-essential amino acids include, but are not limited to substitutions with alanine, glutamic acid, or a methyl amino acid.

Another example of modification of the Der p VII protein is substitution of cysteine residues preferably with alanine, serine, threonine, leucine or glutamic acid residues to minimize dimerization via disulfide linkages. In addition, amino acid side chains of fragments of the protein of the invention can be chemically modified. Another modification is cyclization of the protein.

In order to enhance stability and/or reactivity, the Der p VII protein can be modified to incorporate one or more polymorphisms in the amino acid sequence of the protein allergen resulting from any natural allelic variation. Additionally, D-amino acids, non-natural amino acids, or non-amino acid analogs can be substituted or added to produce a modified protein within the scope of this invention. Furthermore, the Der p VII protein can be modified using polyethylene glycol (PEG) according to the method of A. Sehon and co-workers (Wie et al., supra) to produce a protein conjugated with PEG. In addition, PEG can be added during chemical synthesis of the protein. Other modifications of the Der p VII protein include reduction/alkylation (Tarr in: *Methods of Protein Microcharacterization*, J. E. Silver ed., Humana Press, Clifton N.J. 155–194 (1986)); acylation (Tarr, supra); chemical coupling to an appropriate carrier (Mishell and Shiigi, eds, *Selected Methods in Cellular Immunology*, W H Freeman, San Francisco, Calif. (1980), U.S. Pat. No. 4,939,239; or mild formalin treatment (Marsh (1971), *Int. Arch. of Allergy and Appl. Immunol.* 41:199–215).

To facilitate purification and potentially increase solubility of the Der p VII protein, it is possible to add an amino acid reporter group to the protein backbone. For example, hexa-histidine can be added to the protein for purification by immobilized metal ion affinity chromatography (Hochuli, E. et al., (1988) *Bio/Technology* 6:1321–1325). In addition, to facilitate isolation of Der p VII protein free of irrelevant sequences, specific endoprotease cleavage sites can be introduced between the sequences of the reporter group and the protein or peptide. In order to successfully desensitize an individual to the Der p VII protein or related allergen, it may be necessary to increase the solubility of the protein by adding functional groups to the protein, or by omitting hydrophobic regions of the protein.

To potentially aid proper antigen processing of T-cell epitopes within the Der p VII protein, canonical protease sensitive sites can be engineered between regions, each comprising at least one T-cell epitope via recombinant or synthetic methods. For example, charged amino acid pairs, such as KK or RR, can be introduced between regions within a protein or fragment during recombinant construction thereof. The resulting peptide can be rendered sensitive to cleavage by cathepsin and/or other trypsin-like enzymes which would generate portions of the protein containing one or more T-cell epitopes. In addition, such charged amino acid residues can result in an increase in the solubility of the protein.

Site-directed mutagenesis of a nucleic acid encoding Der p VII can be used to modify the structure of the protein by methods known in the art. Such methods may, among others, include polymerase chain reaction (PCR) with oligonucleotide primers bearing one or more mutations (Ho et al., (1989) *Gene* 77:51–59) or total synthesis of mutated genes (Hostomsky, Z. et al., (1989) *Biochem. Biophys. Res. Comm* 161:1056–1063). To enhance recombinant protein expression, the aforementioned methods can be applied to change the codons present in the cDNA sequence of the invention to those preferentially utilized by the host cell in which the recombinant protein is being expressed (Wada et al., supra).

Another aspect of the invention pertains to an antibody specifically reactive with Der p VII. The antibodies of this invention can be used to standardize allergen extracts or to isolate the naturally-occurring or native form of Der p VII. For example, by using isolated Der p VII protein based on the cDNA sequence of Der p VII, anti-protein/anti-peptide antisera or monoclonal antibodies can be made using standard methods. A mammal such as a mouse, a hamster or rabbit can be immunized with an immunogenic form of the isolated Der p VII protein (e.g., Der p VII protein or antigenic fragment which is capable of eliciting an antibody response). Techniques for conferring immunogenicity on a protein or peptide include conjugation to carriers or other techniques well known in the art. The Der p VII protein or fragment thereof can be administered in the presence of adjuvant. The progress of immunization can be monitored by detection of antibody titers in plasma or serum standard ELISA or other immunoassay can be used with the immunogen as antigen to assess the levels of antibodies.

Following immunization, anti-Der p VII antisera can be obtained and, if desired, polyclonal anti-Der p VII antibodies isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, for example the hybridoma technique originally developed by Kohler and Milstein, (*Nature* (1975) 256:495–497) as well as other techniques such as the human B-cell hybridoma technique (Kozbar et al., *Immunology Today* (1983) 4:72) and the EBV-hybridoma technique to produce human monoclonal antibodies (Cole et al., *Monoclonal Antibodies and Cancer Therapy* (1985) Alan R. Liss, Inc. pp. 77–96). Hybridoma cells can be screened immunochemically for production of antibodies specifically reactive with the Der p VII protein and the monoclonal antibodies isolated.

The term antibody as used herein is intended to include fragments thereof which are also specifically reactive with the Der p VII protein or portion thereof. Antibodies can be fragmented using conventional techniques and the fragments screened for utility in the same manner as described above for whole antibodies. For example, F(ab')$_2$ fragments can be generated by treating antibody with pepsin or papain. The resulting F(ab')$_2$ fragment can be treated to reduce disulfide bridges to produce Fab' fragments. The antibody of the present invention is further intended to include bispecific and chimeric molecules having an anti-Der p VII portion.

A further aspect of this invention pertains to a purified protein consisting essentially of Der p VII. The term purified Der p VII protein is defined as the naturally-occurring or native protein allergen essentially free of all other mite protein allergens. Purified Der p VII protein can be isolated from house dust mite extract by, for example, affinity chromatography with an antibody of the invention as described herein such as an antibody specifically reactive with the recombinant or synthetic Der p VII protein of the invention. Such purified Der p VII protein may exist as different glycosylation products of the protein or may represent isoforms of Der p VII having a molecular weight of about 29 kd, about 27 kd or about 24 kd.

Another aspect of this invention provides T-cell clones and soluble T-cell receptors specifically reactive with Der p VII. Monoclonal T-cell populations (i.e., T-cells genetically identical to one another and expressing identical T-cell receptors) can be derived from an individual sensitive to Der p VII, followed by repetitive in vitro stimulation with Der p VII protein in the presence of MHC-matched antigen-presenting cells. Single Der p VII MHC responsive cells can then be cloned by limiting dilution and permanent lines expanded and maintained by periodic in vitro restimulation. Alternatively, Der p VII specific T-T hybridomas can be produced by a technique similar to B cell hybridoma production. For example, a mammal, such as a mouse, is immunized with Der p VII, T-cells purified and fused with an autonomously growing T-cell tumor line. From the resulting hybridomas, cells responding to Der p VII are selected and cloned. Procedures from propagating monoclonal T-cell populations are described in *Cellular and Molecular Immunology* (Abul K. Abbas et al. ed.), W. B. Saunders Company, Philadelphia, Pa. (1991) page 139. Soluble T-cell receptors specifically reactive with der p VII can be obtained by immunoprecipitation using an antibody against the T-cell receptor as described in *Immunology: A Synthesis* (Second Edition), Edward S. Golub et al., ed., Sinauer Associates, Inc., Sunderland, Mass. (1991) pages 366–269.

T-cell clones specifically reactive with Der p VII can be used to isolate and molecularly clone the gene encoding the relevant T-cell receptor. In addition, a soluble T-cell receptor specifically reactive with Der p VII can be used to interfere with or inhibit antigen-dependent activation of the relevant T-cell subpopulation. For example, by administration to an individual sensitive to Der p VII. Antibodies specifically reactive with such a T-cell receptor can be produced according to the techniques described herein. Such antibodies can be used to block or interfere with the T-cell interaction with peptides presented by MHC.

Isolated Der p VII, or preferred antigenic fragments thereof, when administered to an individual sensitive to house dust mites are capable of modifying the B-cell response, T-cell response, or both the B-cell and the T-cell response of the individual to the allergen. As used herein, modification of the allergic response of an individual to a house dust mite allergen can be defined as non-responsiveness or diminution in symptoms to the allergen, as determined by standard clinical procedures (See e.g., Varney e al, (1990) *British Medical Journal* 302:265–269), including diminution in house dust mite induced asthmatic symptoms. As referred to herein, a diminution in symptoms includes any reduction in the allergic response of an individual to the allergen following a treatment regimen with a peptide or protein of the invention. This diminution in symptoms may be determined subjectively (e.g., the patient feels more comfortable upon exposure to the allergen), or clinically, such as with a standard skin test.

The isolated Der p VII protein can be used in methods of diagnosing, treating, and preventing allergic reactions to a house dust mite allergen or a cross-reactive protein allergen. Thus, the present invention provides therapeutic compositions comprising a therapeutically active amount of Der p VII protein and a pharmaceutically acceptable carrier. Administration of the therapeutic compositions of the present invention to an individual to be desensitized can be carried out using known procedures, at dosages and for periods of time effective to reduce sensitivity (i.e., reduce the allergic response) of the individual to house dust mite. A therapeutically active amount of Der p VII protein may vary according to factors such as the degree of sensitivity of the individual to house dust mite, the age, sex, and weight of the individual, and the ability of the Der p VII protein to elicit an antigenic response in the individual. Dosage regima may be adjusted to provide the optimum therapeutic response. For example, several divided doses may be administered daily or the dose may be proportionally reduced as indicated by the exigencies of the therapeutic situation.

The active compound (i.e., Der p VII protein) may be administered in a convenient manner such as by injection (subcutaneous, intravenous, etc.), oral administration, inhalation, transdermal application, or rectal administration. Depending on the route of administration, the active compound may be coated in a material to protect the compound from the action of enzymes, acids and other natural conditions which may inactivate the compound. If the active compound is administered by injection, for example, about 1 $\mu$g–3 mg and preferably from about 20 $\mu$g–500 $\mu$g of active compound (i.e., Der p VII protein) per dosage unit may be administered.

To administer Der p VII protein by other than parenteral administration, it may be necessary to coat the protein or peptide with, or co-administer the protein with, a material to prevent its inactivation. For example, Der p VII protein may be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water CGF emulsions as well as conventional liposomes (Strejan et al., (1984) *J. Neuroimmunol.* 7:27). For purposes of inducing T-cell anergy, the therapeutic composition is preferably administered in non-immunogenic form, e.g., one that does not contain adjuvant.

The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene gloycol, and the like), suitable mixtures thereof, and vegetable oils. The proper fluidity can be maintained, for example, by the use of a coating such as licithin, by the maintenance of the required particle size in the case of dispersion and by the use of surfactants. Prevention of the action of microorganisms can be achieved by various antibacterial and antifungal agents, for example, parabens, chlorobutanol, phenol, asorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating active compound (i.e., Der p VII protein) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., protein) plus any additional desired ingredient from a previously sterile-filtered solution thereof.

When Der p VII protein is suitably protected, as described above, the protein may be orally administered, for example, with an inert diluent or an assimilable edible carrier. The protein and other ingredients may also be enclosed in a hard or soft shell gelatin capsule, compressed into tablets, or incorporated directly into the individual's diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit contains between from about 10 μg to about 200 mg of active compound.

As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

The present invention also provides a composition comprising at least two antigenic fragments of Der p VII (e.g., a physical mixture of at least two peptides), each having T cell stimulating activity. Such compositions can be administered to an individual in the form of a therapeutic composition with a pharmaceutically acceptable carrier as hereinbefore described. A therapeutically active amount of one or more of such compositions can be administered simultaneously or sequentially to an individual sensitive to a house dust mite allergen to treat such sensitivity.

The Der p VII cDNA (or the MRNA which served as a template during reverse transcription), or a portion thereof, can be used to identify similar nucleic acid sequences in any variety or type of animal and, thus, to molecularly clone genes which have sufficient sequence homology to hybridize to the Der p VII cDNA or mRNA, or portion thereof. For example, proteins with substantial nucleotide sequence homology with the Der p VII cDNA could possibly be identified in *Dermatophagoides farinae* or other related mite species. Thus, the present invention includes not only Der p VII, but also other proteins which may be allergens encoded by DNA which hybridizes to DNA of the present invention.

Isolated allergenic proteins, or fragments thereof, that are immunologically related to Der p VII, such as by antibody cross-reactivity or T-cell cross-reactivity, other than those already identified, are within the scope of the invention. Such proteins or fragments thereof bind antibodies specific for the protein and peptides of the invention, or stimulate T-cells specific for the protein and peptides of this invention.

Isolated Der p VII protein (i.e., Der p VII produced recombinantly or by chemical synthesis) is free of all other mite proteins and, thus, is useful in the standardization of allergen extracts which are key reagents for the diagnosis and treatment of house dust mite hypersensitivity. In addition, such protein is of a consistent, well-defined composition and biological activity for use in preparations which can be administered for therapeutic purposes (e.g., to modify the allergic response of an individual sensitive to house dust mite). Such proteins can also be used to study the mechanism of immunotherapy of *D. pteronyssinus* allergy and to design modified derivatives or analogs useful in immunotherapy.

Work by others has shown that high doses of allergen extracts generally produce the best results during immunotherapy (i.e., best symptom relief). However, many patients are unable to tolerate large doses of such extracts due to systemic reactions elicited by the allergens and other components within these preparations. The isolated Der p VII protein of the invention has the advantage of being free of all other mite protein. Thus, such protein can be administered for therapeutic purposes.

It is now also possible to design an agent or a drug capable of blocking or inhibiting the ability of a house dust mite allergen to induce an allergic reaction in sensitive individuals. Such agents could be designed, for example, in such a manner that they would bind to relevant anti-Der p VII IgE molecules, thus preventing IgE-allergen binding, and subsequent mast cellibasophil degranulation. Alternatively, such agents could bind to cellular components of the immune system, resulting in suppression or desensitization of the allergic responses to house dust mite allergens. A non-restrictive example of this is the use of antigenic fragments of Der p VII including B- or T-cell epitope, or modifications thereof, based on the cDNA protein structure of Der p VII to suppress the allergic response to a house dust mite allergen. This could be carried out by defining the structures of fragments encoding B- and T-cell epitopes which affect B- and T-cell function in in vitro studies with blood components from individuals sensitive to house dust mite.

Der p VII protein or antibodies of the present invention can also be used for detecting and diagnosing sensitivity to house dust mite. For example, this could be done by combining blood, or blood products, obtained from an individual to be assessed for sensitivity to house dust mite with a Der p VII protein or one or more antigenic fragements thereof, under conditions appropriate for binding of components in the blood (e.g., antibodies, HLA molecules, T-cells and B-cells) with the protein or fragment, and determining the extent to which such binding occurs. Other diagnostic methods for allergic diseases which the protein fragment or antibodies of the present invention can be used include radio-allergosorbent test (RAST), paper radioimmunosorbent test (PRIST), enzyme linked immunosorbent assays (ELISA), radioimmunoassays (RIA), immuno-radiometric assays (IRMA), luminescence immunoassays (LIA), histamine release assays and IgE immuoblots.

The invention is further illustrated by the following examples which should not be construed as firther limiting the subject invention. The contents of all references and published patent applications cited throughout this application are hereby incorporated by reference.

EXAMPLE 1

Isolation of clone HD6 from a λgt11 cDNA library

A λgt11 cDNA library was prepared from live adult *Dermatophagoides pteronyssinus* purchased from the Commonwealth Serum Laboratories, Parkville, Australia (Thomas, W., et al., *Int Arch Allergy Appl Immunol* (1988) 85:127–9). The library was prepared according to Chua et al. (*J. Exp. Med.* (1988) 167:175–182) based upon the method of Young and Davis (*Proc. Natl. Acad. Sci. USA* (1983) 80:1194–1198) and Gubler and Hoffman *Gene* (1983) 25:263–299). Polyadenylated mRNA was isolated from a *D. pteronyssinus* culture and cDNA synthesized by the RNaseH method (Gubler and Hoffman, supra) using a kit (Amersham International, Bucks). After the addition of EcoRI linkers the cDNA was ligated into λgt11 and plated in *E. coli* Y1090 (r-) (Promega Biotec, Madison, Wis.) to produce a library of $5 \times 10^5$ recombinants.

Allergic serum was used to probe the λgt11 library. IgE plaque immunoassays were conducted by a standard procedure (Chua, K. Y., et al., *Int Arch Allergy Appl Immunol* (1990) 91:118–23) using 20 000 pfu on 14.5 cm petri dishes. Briefly, an overnight culture of *E. coli* Y1090 (Huynh, T. V. et al. *Constructing and Screening cDNA Libraries in gt*10 *and gt*11 *in: A Practical Approach*, Oxford IRL Press, 1986, pp 48–78) was diluted 1/50 in L broth and incubated at 37° C. to an $OD_{650}$ of 0.6. The bacteria were pelleted and resuspended in 400 μl for every 50 ml of broth. For 14.5-cm Petri dishes, 300 μl of Y1090 were incubated with $10^4$ pfu phage for 30 minutes at room temperature and then plated on LB agar in 9 ml of 0.7% agar overlay and incubated for 3 hours at 42° C. (when plaques usually become visible). At this time a nitrocellulose filter, which had been saturated with 10 mM isopropyl β-D-thiogalactoside and dried, was placed on top of the lawn. The incubation continued overnight at 37° C. The filter was then removed and washed in 0.01 M Tris-hydrochloride, 0.15 M NaCl, 0.05% TWEEN™ 20 (polyoxyethylene 20 sorbitan monolaurate, available from ICI Americas Inc. of Wilmington, Del.) 20 v/v, pH 8, (TNT) buffer with gentle rocking for 20 minutes. The filter was then incubated with sera from mite allergic children for 2 hours at room temperature with rocking and then washed three times for 30 minute periods with TNT. The sera used was first diluted 50:50 with an *E. coli* extract (Huynh et al., supra), incubated overnight then clarified by centrifugation (3,000 g 10 minutes). Non-fat milk and sodium azide were added to 5 and 0.02%, respectively. To develop the IgE reactivity the filter was rocked in a solution of $^{125}$I-labelled anti-IgE for 2 hours at room temperature followed by three 30-minute washes with TNT. The anti-IgE was a mouse monoclonal 2.1.5 (available from Silenus Laboratories Pty. Ltd., Hawthorn, Victoria) and was used at 30 ng/ml coupled with $10^5$ dpm/ng $^{125}$I in TNT (Stewart, G. A., et al. *Int. Arch. Allergy Appl. Immunol.* (1988) 86:9–18). It was labelled by the chloramine T method. The filter was autoradiographed with intensifying screens, usually for 48 hours at –70° C.

A λgt11 derived clone HD6 from the *D. pteronyssinus* cDNA library was plaque purified (see Maniati et al. Molecular Cloning: A Laboratory Manual, (1982) Cold Spring Harbor) because it showed high IgE binding activity to a mite allergic serum (obtained from a child attending the allergy clinic at the Taiwan University Hospital, Taipei, R.O.C.) by the plaque radioimmune assay described above. To determine the number of sera with IgE binding for this clone, the λgt11-HD6 was plated at 1 000 pfu on a 90 cm petri dish and a nitrocellulose lift prepared for an immunoassay as outlined in Young and Davis (1983) supra, with modifications as detailed in Chua et al. *Int. Arch. Allergy Appl. Immunol.* (1990) 91:118–123. The filter was cut into segments and IgE immunoassays performed with 20 individual sera obtained from the Royal Children's Hospital Melbourne (Dr. D. Hill) (FIG. 1). Strong reactivity was found with 6 sera and in another series with 8/18. A hyper IgE serum tested at 1 000 IU/ml did not show binding, nor did a serum from a child allergic to only rye grass (see bottom two segments in right-hand column of FIG. 1).

To estimate the size of the IgE binding molecule encoded by the phage, DNA from purified clones was isolated by a polyethyleneglycol precipitation procedure (Chua, K. Y. et al. *J. Exp. Med.* (1988) 167:175–182) and the 812 bp DNA insert found in the λgt11-HD6 was released by EcoRI digestion (Toyobo, Osaka, Japan) and subdloned into the same site in the glutathione-S-transferase fusion vector pGEX-1 (Smith, D. B. et al., *Gene* (1988) 67:31–40) and used to transform *E. coli* TG-1. The protein expressed by this construct was isolated from crude bacterial lysates under non-denaturing conditions by affinity chromatography on immobilized a glutathione (as described in Smith et al. *Gene* (1988) 67:31–40). The fusion protein was then examined by Western blotting. For Western Blot Analysis, proteins were transferred to nitrocellulose (Bio-Rad TRANSBLOT™) by the protocol of Burnette (Burnette, W. N., *Anal Biochem* (1981) 112:195–203) and immunoassays were performed as for the plaque radioimmune assays with allergic sera and $^{125}$I-anti IgE or with rabbit antibodies and $^{125}$I-protein A as described in Greene, W. K., et al., *Int Arch Allergy Appl Immunol* (1990) 92:30–8.

Figure 2:
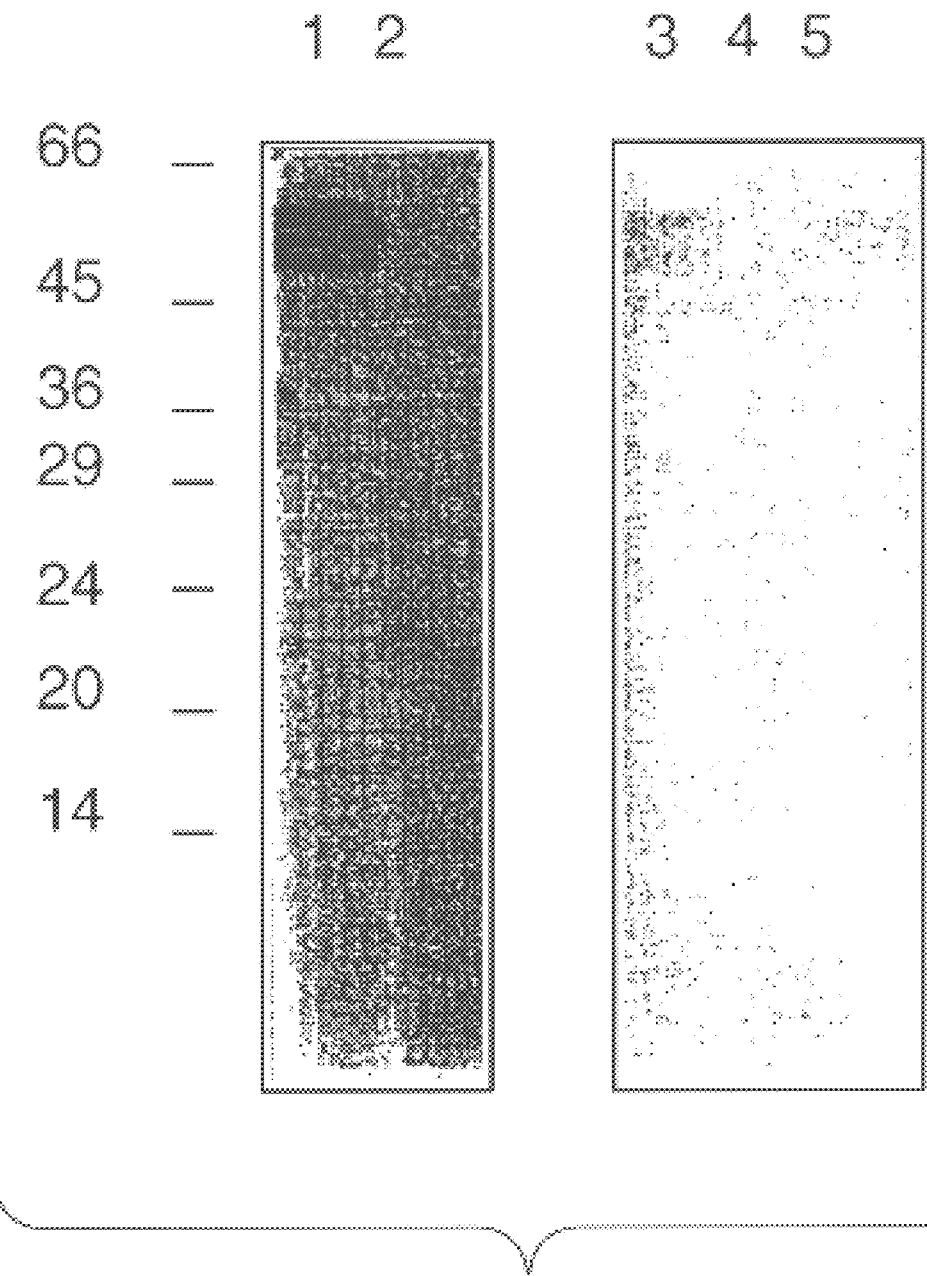
FIG. 2 shows the reactivity of IgE and rabbit anti-house dust mite antibody to purified glutathione-S-transferase fusion product of the HD6 insert cloned into pGEX-1.

Expression in pGEX-1 resulted in a protein(s) which migrated as a doublet with a Mr of 53–55 K and reacted by Western blotting with rabbit anti-house dust mite serum (FIG. 2, lane 1). Two allergic sera reacted with this doublet (FIG. 2, lanes 3 and 5) but not to a hyper IgE serum at 1000 IU/ml (FIG. 2, lane 4) or normal rabbit serum (FIG. 2, lane 2). The IgE binding protein, allowing for the contribution of the 27 K glutathione transferase would therefore be about Mr 27. This, as will be described below, contains residues from the leader sequence and those from the 5' untranslated region.

EXAMPLE 2

DNA Sequence Analysis of Clone HD6

The 812 bp insert of clone HD6 was cloned into the M13 vectors mp18 and mp19 (see Messing *Methods Enzymology* (1983) 101:20) for sequencing performed in both directions using –40, universal and internal primers (Messing, supra). Dideoxynucleotide sequencing (Sambrook, J., et al. *Molecular Cloning. A Laboratory Manual*. 2nd Edition. Cold Spring Harbor: Cold Spring Harbor Laboratory Press, 1989) was performed using a SEQUENASE ™2.0 DNA sequencing kit (IBI, New Haven, USA) with $^{32}$p-dATP and a Biorad SEQUI-GEN™ electrophoresis apparatus. Following sequence analysis with the universal and internal primers, three primers based on the cDNA sequence of Der p VII were produced and sequencing conducted. The sequences of the primers are as follows: (1) GATCCAATTCACTATGAT (bases 119–136 in FIG. 3, SEQ ID NO:3); (2) GGT-GAATTAGACATGCG (bases 272–288 in FIG. 3, SEQ ID NO:4); and (3) TCAATTTTGGATCCAATTTTCGCT (bases 584–607, SEQ ID NO:5).

The DNA insert was found to have 812 bases with an open reading frame beginning at the 5' end, consistent with its expression as a fusion from λgt11 and pGEX-1, and ending at a stop codon TAG (713–715) (FIG. 3). The sequence of the translated protein appeared to begin at the adjacent initiation ATGs at nucleotides 68–70 and 71–73. This is followed by nucleotides encoding a typical, predominantly hydrophobic, leader sequence (Von Hiejne, G. *J. Mol. Biol.* (1985) 184:99–105) predicted to be 17 residues long, and then a sequence encoding a further 198 residues ending at the TAG codon at nucleotides 713–715. This reading frame was confirmed by using PCR (as described in Saiki et al. *Science* (1988) 239:487–491) to clone DNA encoding an antigenic product of the correct Mr in pGEX starting at the predicted N-terminal Asp encoded by nucleotide 119–121. The fusion protein from this construct was produced at far higher yields than the fusion which contained the leader peptide (pGEX-1). The 3' untranslated region contained a polyadenylation signal AATAAA at 765–770 (underlined in FIG. 3) and a polyA tail. A potential N-glycosylation site, Asn Ala Thr, is encoded by nucleotides 518–526 (see FIG. 3 underlined). No homology was found to sequences in the Genpept 71.0, EMBL 30.0 and Swiss-Prot 21 databases. The predicted molecular weight of the translated polypeptide was 23,865 daltons and 22,177 daltons without the leader sequence.

EXAMPLE 3

Nature of the Allergen Der p VII in Mite Extracts

Figure 4:
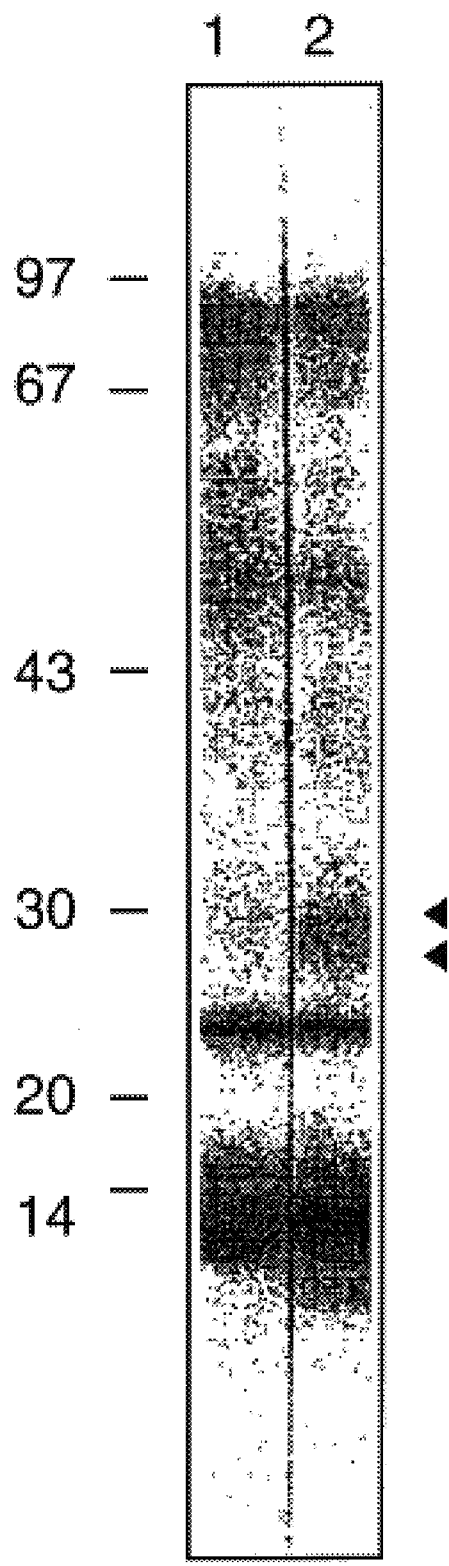
FIG. 4 shows extracts of house dust mites electrophoresed on a 8–18% SDS-PAGE, electroblotted onto nitrocellulose and reacted with pooled allergic serum absorbed with lysates from *E. coli* containing a pGEX-1 vector control (lane 1) or pGEX-1 HD6 (lane 1).

As a first step to identifying the Der p VII native protein allergen, a pool of allergic serum obtained as described previously was absorbed with an equal volume of pGEX-1 HD6 lysate or a control vector lysate (Greene and Thomas *Molec. Immunol.* (1992) 29:259–262). The serum was then used for IgE Western blotting of house dust mite extracts separated by SDS-PAGE performed according to Laemmli (Laemmli, U. K., Nature (1970) 227:680–5) with an 8–18% gradient in 10–12 cm gel assemblies or 13% mini PRO-TEIN™ II electrophoretic apparatus (Bio-Rad, Richmond, Va., USA). For dust mite extracts, samples were loaded at 0.1 mg protein/track. For bacteria, cultures were centrifuged and the pellets suspended at 0.01 of the culture volume and 10 μl added to sample buffer for electrophoresis. Purified proteins were electrophoresed at 2–5 μl/track. Compared to the serum absorbed with vector control (FIG. 4, lane 2), the HD6 fusion protein absorbed serum (FIG. 4, lane 1) showed a loss of reactivity to bands with Mr of 29, 27 and 11.5 K.

To examine this further, rabbit antibodies to the HD6 protein were affinity purified from a hyperimmune serum using nitrocellulose filters lifted from plates confluent with λgt11-HD6 plaques. Briefly, antibodies with specificities for the allergen expressed by the λgt11 clones were isolated from a hyperimmune rabbit anti-*D. pteronyssinus* serum (Greene, W. K., et al., *Int Arch Allergy Appl Immunol* (1990) 92:30–8) (produced by repeated injections into a rabbit of mite extract) by affinity purification using a nitrocellulose filter blotted on a plaque lawn (Ozaki, L. S., et al., *J. Immunol Methods* (1986) 89:213–9) as the absorbant. λgt11 derived phage (clone HD6) were plated at 10 000 pfu per 90 cm petri dishes and overlaid with nitrocellulose saturated with isopropyl-β-D-thiogalactopyranoside (IPTG) under the same conditions used to screen the library. After overnight incubation, the filter was flipped to expose the other side to the lawn and incubated for 2 hours at 37° C. The filter was then washed in the TNT buffer, (0.01 M Tris hydrochloride, 0.15 NaC, 0.05% Tween 20 v/v pH 8.0). One ml of rabbit antiserum which had been incubated overnight in 1 ml of a lysate of λgt11 lysogen was diluted to 20 mls with TNT and skim milk powder added to 5%. Aliquots of 5 ml were then rocked in petri dishes containing the filters for 1 hour at room temperature. The filters were washed three times in TNT and incubated for 15 minutes at room temperature in 0.1 M glycine, 0.15 M NaCl pH2.6 to elute the antibodies. Each 5 ml eluate was then neutralized by adding 650 μl of 100 mM Tris and 1.5 m NaCl, 50 ml 1% sodium azide and 0.25 g skim milk. The solution was dialysed against PBS.

Figure 5:
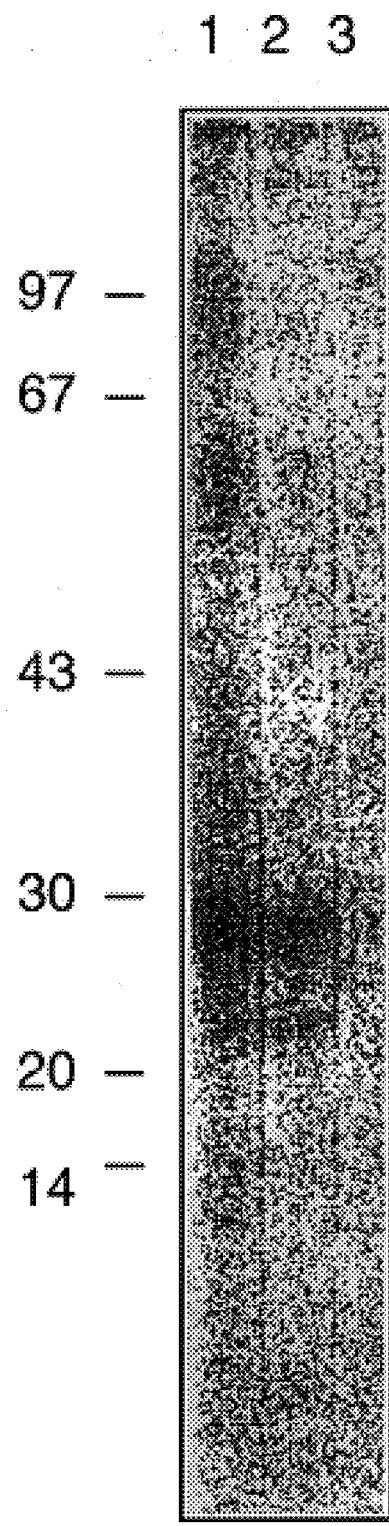
FIG. 5 shows the reactivity of affinity purified anti-HD6 antibodies to *D. pternyssinus* extracts. Rabbit antibodies were affinity purified on nitrocellulose and used to probe a Western blot of mite extracts, electrophoresed on 8–18% SDS-PAGE and developed with $^{125}$I-protein A.

The affinity purified antibody was then absorbed with *E. coli* lysate used to develop Western blots as described, on the house dust mite extract and found to react with bands of Mr 29, 27 and 24 (FIG. 5). The specificity of the reactivity was further checked by absorbing the affinity purified antibodies with a pGEX-HD6 lysate expressing the protein (FIG. 5, lane 3) or a control pGEX construct, pGEX-D15 (FIG. 5, lane 2). The serum absorbed with HD6 (lane 3) lost reactivity to all bands. The affinity purification therefore shows that antibodies to the allergen have specificities for components at Mr 29, 27 and 24 K. The same pattern of multiple binding to that described above with extracts prepared from CSL mites was also found with another extract from Hollister-Stier Laboratories, Spokane, Wash., USA.

The finding that antibodies to the HD6 lysate reacted specifically to at least 3 bands on Western blotting has implications for determining the number of allergens recognized by individual mite allergic patients. The multiple bands were found for the two independent extracts examined and the absorption studies with allergic serum showed that the 29 and 27 K bands had IgE reactivity and that this recombinant molecule appeared to absorb out all of the reactivity to each band. It is not, however, known from this investigation if all patients react with each band. Because the Western analysis was performed using reducing conditions and the bands had Mr greater than that calculated from the translated sequence, the different forms of the allergens may be interpreted as different glycosylation products. This can be confirmed with some caution taken to control for denaturation by the deglycosylation procedures. The pattern nevertheless indicates that the number of allergic specificities is less than that indicated by electrophoretic procedures, a significant observation for immunotherapeutic strategies using purified, recombinant or peptide allergens. Alternatively, the different Mr bands reacting with the anti-HD6 antibody may indicate the presence of related or cross reactive allergens.

Those skilled in the art will recognize or be able to ascertain using no more than routine experimentation, numerous equivalents to the specific embodiments described herein. Such equivalents are considered to be within the scope of this invention and are encompassed by the following claims.

What is claimed is:

1. An isolated Group VII protein allergen of *Dermataphagoides pteronysinus*, Der p VII, comprising the amino acid sequence shown in FIG. 3 (SEQ ID NO:2), wherein said protein allergen is produced recombinantly in a heterologous host cell, or by chemical sinthesis, and is free of all other dust mite proteins.

2. An isolated protein allergen of claim 1 encoded by the nucleic acid shown in FIG. 3 (SEQ ID NO 1).

3. A therapeutic composition comprising an isolated protein of claim 2 and a pharmaceutically acceptable carrier.

4. A therapeutic composition comprising a therapeutically active amount of a Der p VII protein allergen of claim 1 and a pharmaceutically acceptable carrier.

5. An isolated Group VII protein allergen of *Dermataphagoides pteronyssinus*, Der p VII, comprising amino acid residues 18–215 of FIG. 3 (SEQ ID NO:2), wherein said protein allergen is produced recombinantly in a heterologous host cell, or by chemical synthesis, and is free of all other dust mite proteins.

6. A therapeutic composition comprising a therapeutically active amount of a Der p VII protein allergen of claim 5 and a pharmaceutically acceptable carrier.

7. An isolated protein allergen which is a naturally occurring polymorphic variant of a Group VII protein allergen of *Dermataphagoides pteronyssinus*, Der p VII, said isolated protein allergen comprising an amino acid sequence which differs from the amino acid sequence shown in FIG. 3 (SEQ ID NO: 2), or the mature portion thereof, due to natural allelic variation, wherein said protein allergen is produced recombinantly in a heterologous host cell, or by chemical synthesis, and is free of all other dust mite proteins.

8. An isolated protein allergen of claim 7, encoded by a nucleic acid which differs by about 3–4% of the nucleotides from the nucleic acid shown in FIG. 3 (SEQ ID NO: 1).

9. A therapeutic composition comprising an isolated protein of claim 7 and a pharmaceutically acceptable carrier.

10. An isolated peptide comprising at least one T cell epitope recognized by a T cell receptor specific for a Der p VII protein allergen having the amino acid sequence shown in FIG. 3 (SEQ ID NO 2), provided the peptide does not comprise said entire Der p VII amino acid sequence, wherein said peptide is produced recombinantly in a heterologous host cell transformed with DNA encoding the peptide, or by chemical synthesis, and wherein said peptide is free of all other dust mite proteins.

11. An isolated peptide of claim 10 wherein the T cell receptor is a human T cell receptor.

12. An isolated peptide of claim 10 further comprising at least one B cell epitope recognized by a B cell specific a Der p VII protein allergen having the amino acid sequence shown in FIG. 3 (SEQ ID NO 2).

13. A diagnostic reagent comprising an isolated Der p VII protein allergen or peptide of any one of claims 1, 5, or 7, or 10, and a carrier or diluent.

14. A diagnostic reagent comprising an isolated peptide of claim 10 and a carrier or diluent.

* * * * *